United States Patent [19]

Obayashi et al.

[11] Patent Number: 4,868,115

[45] Date of Patent: Sep. 19, 1989

[54] ENZYME COMPOSITION

[75] Inventors: Akira Obayashi, Uji; Nobutsugu Hiraoka, Muko; Yukuo Ishizaki, Moriyama; Atsushi Ohshima; Mitsuo Kasai, both of Otsu, all of Japan

[73] Assignee: Takara Shuzo Co., Ltd., Kyoto, Japan

[21] Appl. No.: 72,843

[22] Filed: Jul. 9, 1987

[30] Foreign Application Priority Data

Aug. 4, 1986 [JP] Japan .................. 61-181934

[51] Int. Cl.$^4$ .............................................. C12N 9/96
[52] U.S. Cl. ...................................... 435/188; 435/6; 435/194
[58] Field of Search ................... 435/6, 183, 188, 194

Primary Examiner—Robert A. Wax
Attorney, Agent, or Firm—Wenderoth, Lind & Ponack

[57] ABSTRACT

An enzyme composition comprising a series of enzymes used for DNA base sequence analysis by gel electrophoresis and a dihydric alcohol.

7 Claims, No Drawings

ENZYME COMPOSITION

This invention relates to enzyme compositions used in genetic engineering. More particularly, it relates to compositions comprising a series of enzymes used for DNA base sequence analysis.

A method for analyzing the structure and function of a gene has recently been developed (hereinafter referred to as "dideoxy method"), in which the base sequence of that particular gene is determined by utilizing a specific enzyme reaction.

In this method, a primer is linked to a single-stranded DNA purified by various techniques and DNA synthesis is performed using a member selected from a group of enzymes having DNA polymerase activity, in which a four (or three) step reaction involving, as substrate, four types of deoxytriphosphates and a dideoxy-triphosphate (an inhibitor) is allowed to proceed simultaneously. Thus the reaction terminates the moment the above inhibitor is incorporated. The DNA thus synthesized having a limited chain length is then denatured and subjected to electrophoresis on a denaturing polyacrylamide gel. The base sequence can be determined by detecting the DNA fragments thus separated and comparing their chain lengths.

The enzymes having DNA polymerase acitvity used in this dideoxy method are stored at −20° C. and marketed in the form of a composition containing 50 to 65% glycerol for ease of handling and to ensure storage stability.

This type of enzyme composition, however, has the problem that it gives bent electrophoresis band patterns when applied to DNA's composed of about 350 or more bases, making base sequence analysis in this region impossible.

The object of this invention is to provide enzyme compositions free from such a problem.

In summary, this invention relates to enzyme compositions comprising enzymes used for DNA base sequence analysis by gel electrophoresis and a dihydric alcohol.

Any enzymes employed for DNA base sequence analysis by gel electrophoresis may be used as enzymes of this invention. These include Escherichia coli DNA polymerase I, Klenow enzyme [Pro. Natl. Acad. Sci. USA, 80, 1830–1834 (1983)], and reverse transcriptase.

As examples of the gel used in gel electrophoresis there may be mentioned polyacrylamide, agarose and denaturing gels therefrom.

The dihydric alcohol used in this invention is selected, for example from alkylene glycols and polyalkylene glycols. Illustrative examples include ethylene glycol, diethylene glycol and propylene glycol. These may be used either alone or in combination.

The concentration of the dihydric alcohol in the enzyme compositions of this invention is not critical, but is usually in the range from 30 to 75% (V/V), more preferably from 40 to 60%.

In order for an enzyme to be stably stored, use of a specific buffer solution, sugar, reducing agent and surface-active agent is essential. In the stabilized enzyme composition of this invention, too, each of the enzymes involved may be combined with proper additives; Klenow enzyme, for example, is usually combined with 50 mM potassium phosphate buffer (pH 6.5) and 10 mM β-mercaptoethanol.

The following examples further illustrate the invention but are not intended to limit its scope.

EXAMPLE 1

A 50 mM potassium phosphate buffer (pH 6.5) containing 2 U/μl Klenow enzyme (Takara Shuzo Co., Ltd.) and 10 mM β-mercaptoethanol were mixed with 50 vol % ethylene glycol, 50 vol % diethylene glycol and 50 vol % propylene glycol each, giving three types of enzyme compositions.

Separately, a similar enzyme composition containing 50 vol % glycerol in place of a dihydric alcohol was prepared.

These compositions were stored at −20° C. for one month to examine their storage stability. The result is shown in Table 1 (the activity immediately after preparation is taken as 100%).

TABLE 1

| Storage period (day) | 0 | 3 | 12 | 28 |
|---|---|---|---|---|
| Ethylene glycol composition | 100 | 95 | 101 | 101 |
| Diethylene glycol composition | 100 | 100 | 100 | 99 |
| Propylene glycol composition | 100 | 100 | 100 | 98 |
| Glycerol composition | 100 | 109 | 109 | 109 |

As can be seen from the table, no drop in activity was observed in any of the compositions.

EXAMPLE 2

An enzyme composition which comprises a 200 mM potassium phosphate buffer solution (pH 7.2) containing 20 U/μl reverse transcriptase (Takara Shuzo Co., Ltd.), 50 vol % propylene glycol, 2 mM dithiothreitol and 0.2 vol % Nonidet P-40 (Nakarai Chemicals) was prepared, and its storage stability was examined in the same manner as in EXAMPLE 1. No drop in activity was observed after about one month.

EXAMPLE 3

Base sequence analysis by the dideoxy method was performed using the Klenow enzyme compositions prepared in EXAMPLE 1. In this technique, [α-$^{32}$P]deoxycytidine-triphosphate (hereinafter abbreviated as [α-$^{32}$P]dCTP; product of Amarsham Inc.; approximately 400 Ci/mmol, 10 mCi/ml) was used in the enzymatic reaction, and 95% desalted formamide containing 0.1% xylene-cyanol and 0.1% Bromophenol Blue was employed as reaction stopping solution.

DNA that serves as substrate of enzymatic reaction was first synthesized as follows.

M13 single-stranded phage DNA (5 μl, 0.5 pmol) was mixed with 1 μl of a primer and 1.5 μl of a concentrated buffer soltion (containing 70 mM Tris-HCl, pH:7.5, 70 mM MgCl$_2$, 200 mM NaCl and 1 mM EDTA), and distilled water was added to the mixture to make up 12 μl. The resulting solution was heated in a thermostatic bath held at 60° C. for 20 minutes to link the primer to the phage DNA. [α$^{32}$P]dCTP (2 μl) and Klenow enzyme stabilized by ethylene glycol (1 μl; 2U) were carefully admixed, and the mixture thus obtained (3.5 μl each) was added to each of the four mixtures (a deoxytriphosphate plus dideoxy-triphosphate), and the reaction was allowed to proceed at 25° C. for 20 minutes. A Chase mixture (containing 1 mM each of dATP, dCTP, dGTP and TTP) was added to each, and the reaction was continued for 20 minutes. After terminating the reaction by addition of 6 μl of reaction stopping solution, the reaction mixture was heated at 95° C. for three minutes to denature the DNA. A solution of the DNA thus obtained having a limited chain length (4μl) was put on a denaturing polyacrylamide gel (8%) containing 7M urea [also containing 89 mM trishydroxymethylaminomethane, 89 mM boric acid and 10 mM ethylenediaminetetraacetic acid buffer solution (pH 8.3)], and electrophoresis was conducted for four hours at a voltage of 40 to 50 V/cm. At the end of electrophoresis, the gel was vacuum-dried at an elevated temperature, the dry gel was placed on a sheet of X-ray film to effect exposure (at −70° C., 15 hrs.), and the exposed X-ray film was developed by a usual method, giving a DNA base sequence ladder.

Bent electrophoresis band patterns were observed for fragments composed of more than about 350 bases with the glycerol-containing Klenow enzyme, while no such abnormality was noticed with the ethylene-glycol-containing enzyme, giving a sharp electrophoresis diagram up to about 500 bases.

Similar sharp electrophoresis diagrams were obtained for the Klenow enzymes containing diethylene glycol and propylene glycol as well.

EXAMPLE 4

Base sequence analysis by the dideoxy method was performed in a similar manner as in EXAMPLE 3 using the reverse transcriptase compositions prepared in Example 2. DNA that serves as substrate of enzymatic reaction was first synthesized as follows. M13 single-stranded phage DNA (5 μl, 0.5 pmol) was mixed with 1 μl of a primer and 1.5 μl of a concentrated buffer solution (containing 0.1M Tris-HCl, pH 8.0 and 70 mM $MgCl_2$), and distilled water was added to the mixture to make up 11 μl. The resulting solution was heated in a thermostatic bath held at 60° C. for 20 minutes to link the primer to the phage DNA. [α-$^{32}$P]dCTP (2 μl) and reverse transcriptase (1 μl; 20U) stabilized by dithiothreitol (0.2 μl) and propylene glycol were carefully admixed, and the mixture thus obtained (3.5 μl each) was added to each of the four mixtures (a deoxy-triphosphate plus dideoxytriphosphate, 2 μl each), and the reaction was allowed to proceed at 42° C. for 15 minutes. A Chase mixture (containing 1 mM each of dATP, dCTP, dGTP and dTTP) was added to each, and the reaction was continued for 15 minutes. After terminating the reaction by addition of 6 μl of reaction stopping solution, the reaction mixture was heated at 95° C. for three minutes to denature the DNA. A solution of the DNA thus obtained having a limited chain length (4 μl) was put on a denaturing polyacrylamide gel (8%) containing 7M urea [also containing 89 mM tris-hydroxymethylaminomethane, 89 mM boric acid and 10 mM ethylenediaminetetraacetic acid buffer solution (pH 8.3)], and electrophoresis was conducted for four hours at a voltage of 40 to 50 V/cm. At the end of elecrtrophoresis, the gel was vacuum-dried at an elevated temperature, the dry gel was placed on a sheet of X-ray film at 70° C. for 15 hours to effect exposure, and the exposed X-ray film was developed by a usual method, giving a DNA base sequence diagram.

Bent electrophoresis band patterns were observed for fragments composed of more than about 350 bases with the glycerol-containing transcriptase, while no such abnormality was noticed with the propylene-glycol-containing enzyme composition, giving a sharp electrophoresis diagram up to about 500 bases.

Similar sharp electrophoresis diagrams were obtained for the transcriptase containing ethylene glycol, diethylene glycol and propylene glycol as well.

As is apparent from the foregoing, use of the enzyme compositions of this invention makes it possible to analyze base sequence of DNA's composed of more than about 350 bases.

What we claim is:

1. An enzyme composition comprising a series of enzymes used for DNA base sequence analysis by gel electrophoresis and a dihydric alcohol.

2. The enzyme composition as defined in claim 1, wherein said dihydric alcohol is an alkylene glycol or a polyalkylene glycol.

3. The enzyme composition as defined in claim 1, wherein said dihydric alcohol is ethylene glycol, diethylene glycol or propylene glycol.

4. The enzyme composition as defined in any of claim 1, wherein the concentration of said dihydric alcohol is in the range from 30%(v/v) to 75%(v/v).

5. The enzyme composition as defined in claim 2, wherein said dihydric alcohol is ethylene glycol, diethylene glycol or propylene glycol.

6. The enzyme composition as defined in claim 2, wherein the concentration of said dihydric alcohol is in the range from 30%(v/v) to 75%(v/v).

7. The enzyme composition as defined in claim 3, wherein the concentration of said dihydride alcohol is in the rangefrom 30%(v/v) to 75%(v/v).

* * * * *